United States Patent [19]

Fridd et al.

[11] Patent Number: 4,601,902
[45] Date of Patent: Jul. 22, 1986

[54] COMPOSITIONS AND PROCESS FOR TREATING HAIR

[75] Inventors: Petrina F. Fridd, Penarth; Rosemary M. Taylor, Barry; Michael P. Hill, Saint Lythans, all of Wales

[73] Assignee: Dow Corning Ltd., Barry, Wales

[21] Appl. No.: 632,357

[22] Filed: Jul. 19, 1984

[30] Foreign Application Priority Data

Jul. 30, 1983 [GB] United Kingdom ............... 8320603

[51] Int. Cl.$^4$ ............................................. A61K 7/06
[52] U.S. Cl. .................................... 424/70; 252/106; 424/DIG. 4
[58] Field of Search ................................. 424/70, 184

[56] References Cited

U.S. PATENT DOCUMENTS 4,185,087  1/1980  Morlino .............................. 424/70

FOREIGN PATENT DOCUMENTS

| 677857 | 1/1964 | Canada | 424/184 |
| 2912484 | 10/1980 | European Pat. Off. | 424/70 |
| 0095238 | 11/1983 | European Pat. Off. | 424/70 |
| W 11605 | 5/1956 | Fed. Rep. of Germany | 424/70 |
| 2033191 | 12/1970 | France | 424/184 |
| 0028906 | 2/1980 | Japan | 424/184 |
| 0004709 | 1/1983 | Japan | 424/70 |
| 992087 | 5/1965 | United Kingdom | 424/70 |
| 1158139 | 7/1969 | United Kingdom | 424/70 |
| 2039512 | 8/1980 | United Kingdom | 424/70 |
| 2058103A | 4/1981 | United Kingdom | 424/70 |

Primary Examiner—Dale R. Ore
Attorney, Agent, or Firm—George A. Grindahl; James E. Bittell

[57] ABSTRACT

A hair treating composition which comprises (1) a silane or a polydiorganosiloxane having quaternary ammonium substituted groups attached to silicon, (2) a polydiorganosiloxane having silicon-bonded substituents which are amino-substituted hydrocarbon groups, (3) one or more surfactants, and (4) water. The compositions can be formulated as e.g. hair conditioning agents or as shampoos.

7 Claims, No Drawings

COMPOSITIONS AND PROCESS FOR TREATING HAIR

This invention relates to compositions for treating hair to improve the manageability, softness and appearance thereof and also relates to a process for treating hair with such compositions.

It has been well-known for many years to employ additives in shampoos to improve the condition and appearance of the hair after washing. It has also been well-known, particularly in connection with hair grooming products for ladies to achieve an improvement in appearance, condition and manageability of the hair by the application of hair conditioning products immediately after shampooing. Such conditioners are generally based on a cationic surfactant in conjunction with certain fatty materials e.g. mineral oil, lanolin or long chain alcohols, and render the hair more lustrous, easy to comb and less susceptible to 'fly away' resulting from static electricity.

More recent developments in the formulation of conditioners have involved the use of silicones as components of hair grooming/conditioner formulations. British Pat. No. 992 087 discloses a process for treating hair to improve its appearance manageability and softness which comprises submitting the hair to the action of an oil-in-water emulsion of a polymerised organosiloxane. British Patent No. 1 158 139 discloses hair dressing compositions containing dimethylpolysiloxanes, particularly cyclic dimethylsiloxanes, having a boiling point within the range from 170° C. to 265° C. GB 2 058 103A discloses compositions for conditioning hair which comprise on a weight basis (a) from about 0.2 to about 10% of a silicone polymer,
(b) from about 0.01 to about 10% of at least one cationic polymer; and
(c) an aqueous carrier.

U.S. Pat. No. 4,185,087 discloses a method of conditioning hair which comprises applying to the hair an effective amount of a composition containing (A) from about 0.1 to about 10 weight percent of a quaternary nitrogen derivative of a trialkylamino hydroxy organosilicon compound, (B) from about 75 to about 99.9 percent water; and (C) from about 0 to about 30 weight percent of one or more surfactants.

European Patent Application No. 95 238 discloses compositions for the treatment of hair consisting essentially of a siloxane having substituents that provide attachment to the hair e.g. amino, carboxy, amide or quaternary amino, surfactants, additives that provide freeze-thaw stability and water.

Although considerable development of hair grooming products has taken place there has been a continuing search for improvements in the properties imparted to the hair. Thus, while it has been possible to obtain improved gloss it is desirable that this property be associated with fullness and body in the hair and preferably also with ease of wet and dry combing.

According to this invention there is provided a hair treating composition which comprises (1) an organosilicon compound selected from (a) silanes represented by the general formula

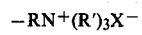

wherein each Q represents an alkyl group having from 1 to 4 carbon atoms, a hydroxyl group or an alkoxy group or alkoxyalkoxy group having less than 12 carbon atoms, R represents a divalent aliphatic hydrocarbon group having from 3 to 10 carbon atoms and composed of carbon, hydrogen and, optionally, oxygen present in the form of ether linkages and/or hydroxyl groups, each R' represents a monovalent hydrocarbon group having from 1 to 18 carbon atoms and X represents a halogen atom, and (b) polydiorganosiloxanes having in the molecule at least one silicon-bonded group represented by the general formula $$-RN^+(R')_3 X^-$$

wherein R, R' and X are as hereinabove defined, at least 40 percent of the total silicon-bonded substituents being methyl groups and any remaining substituents being selected from monovalent hydrocarbon groups having from 2 to 8 carbon atoms, hydroxyl groups and alkoxy and alkoxy-alkoxy groups having less than 12 carbon atoms, (2) a polydiorganosiloxane having in the molecule at least one group represented by the general formula

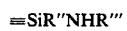

wherein R" represents an alkylene group having from 3 to 8 inclusive carbon atoms and R''' represents a hydrogen atom, an alkyl group having from 1 to 4 inclusive carbon atoms or an aliphatic hydrocarbon group attached to the nitrogen atom through a carbon to nitrogen bond and containing at least one group selected from —NH— and —NHZ groups wherein Z represents a hydrogen atom or an alkyl group having from 1 to 4 carbon atoms, at least 50 percent of the total silicon-bonded substituents being methyl groups and any remaining substituents being selected from monovalent hydrocarbon groups having from 2 to 8 carbon atoms, hydroxyl groups and alkoxy and alkoxyalkoxy groups having less than 12 carbon atoms, (3) one or more surfactants and (4) water.

Also included within the scope of this invention is a process for the treatment of hair which comprises applying thereto a composition as hereinabove defined.

The organosilicon compound which constitutes component (1) of the compositions of this invention may be an organosilane or a polydiorganosiloxane or mixtures of the two. In the general formula of the organosilanes (a) each Q represents an alkyl group having from 1 to 4 carbon atoms, a hydroxyl group or an alkoxy or alkoxyalkoxy group having less than 12 carbon atoms. Preferably each Q is methyl, methoxy, ethoxy or methoxyethoxy. The group R may be for example —(CH$_2$)$_3$—, —(CH$_2$)$_4$—, —CH$_2$CH$_2$CHCH$_3$CH$_2$— or —(CH$_2$)$_6$— but is preferably —(CH$_2$)$_3$— or —CH$_2$CH.CH$_3$CH$_2$—; and each R' may be for example methyl, ethyl, propyl, decyl, tetradecyl or octadecyl. The anion X$^-$ may be Cl$^-$, Br$^-$ or I$^-$ but is preferably Cl$^-$.

In the general formula of the polydiorganosiloxanes 1 (b) R, R' and X are as defined hereinabove with respect to the general formula of the silanes. The polydiorganosiloxanes are linear or substantially linear polymers in which at least 40 percent of the total silicon-bonded substituents are methyl groups. Any other substituents present in addition to the specified quaternary amino and methyl groups are monovalent hydrocarbon groups having from 2 to 8 carbon atoms e.g. ethyl, propyl, vinyl or phenyl, hydroxyl groups, alkoxy groups e.g. methoxy, ethoxy, n-propoxy or alkoxyalkoxy e.g. methoxyethoxy and ethoxyethoxy. Depending on their molecular weight and the proportion of silicon-bonded quaternary groups the polydiorganosiloxanes may vary from freely-flowing liquids to sticky gums. The preferred polydiorganosiloxanes (b) are those having up to about 800 silicon atoms in the molecule. Preferably also the proportion of quaternary-containing substituents lies within the range from 1 per 500 silicon atoms to 1 per silicon atom.

The organosilicon compounds (1) are known materials and may be prepared as described for example in British Patent No. 1 117 592 and British Patent Application No. 2 107 715A. Specific examples of organosilicon compounds (1) are

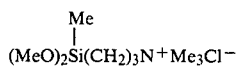

$(MeOCH_2CH_2O)(MeO)_2Si(CH_2)_3N^+Me_2(C_{18}H_{37})Cl^-$
$(Me_3SiO)_3Si(CH_2)_3N^+Me_2(C_{13}H_{27})Cl^-$
$Me_2PrSiCH_2CH.CH_3CH_2N^+Me_2(C_{12}H_{25})Cl^-$ and

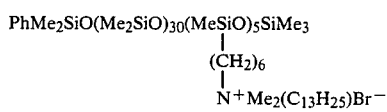

Me, Ph and Pr representing methyl, phenyl and propyl respectively.

Polydiorganosiloxanes (2) are characterised by the presence of at least one amino-containing group $\equiv SiR''NHR'''$ in the molecule. In the general formula defining the said group $R''$ may be e.g. $-(CH_2)_4-$, $-(CH_2)_6-$, $-(CH_2)_8-$ but is preferably $-(CH_2)_3-$ or $-CH_2CH(CH_3)CH_2-$. The substituent $R'''$ may represent hydrogen, lower alkyl e.g. methyl, ethyl or propyl, or may represent an aliphatic hydrocarbon group having therein at least one group selected from the $-NH-$ and $-NHZ$ groups, wherein Z is as herein defined. Examples of such aliphatic hydrocarbon groups are those represented by $-YNH_2$, wherein Y represents a divalent hydrocarbon group e.g. $-CH.CH_3CH_2-$, $-(CH_2)_4$ or $-(CH_2)_5-$, and those represented by $-(CH_2CH_2NH)_aH$ wherein a is an integer, preferably 1 or 2. Polydiorganosiloxanes wherein the $-R''NHR'''$ groups are $-(CH_2)_3NH_2$, $-(CH_2)_3NHCH_2CH_2NH_2$ and $-CH_2CH.CH_3CH_2NHCH_2CH_2NH_2$ are normally more generally available and are therefore preferred. In the polydiorganosiloxane (2) at least 50 percent of the total silicon-bonded substituents are methyl groups, any substituents present in addition to the amino-containing groups and methyl groups being monovalent hydrocarbon groups having from 2 to 8 carbon atoms, hydroxy groups and alkoxy and alkoxyalkoxy groups having less than 12 carbon atoms. Examples of such additional groups are ethyl, propyl, 2,2;4-trimethylphenyl, methoxy, ethoxy and methoxyethoxy.

Polydiorganosiloxanes (2) may vary in consistency from freely flowing liquids to gummy solids but are preferably those having up to about 800 silicon atoms in the molecule. They are, in general, known and commercially available materials.

The compositions of this invention contain at least one surfactant (3) which functions to maintain the organosilicon components (1) and (2) in the dispersed state in the aqueous medium. The nature of the surfactant is not critical; preferably it is cationic, or non-ionic. Examples of surfactants are aliphatic fatty amines and their derivatives e.g. octadecylamine acetate and quaternary ammonium halides, sodium lauryl sulphate, ethylene oxide adducts of octyl or nonyl phenols e.g. octylphenoxypolyethoxyethanol, monoesters of alcohols and fatty acids e.g. glyceryl stearate, sorbitan monolaurate and polyoxyethylenemonostearate, and polyvinyl alcohol.

Depending on the nature and balance of quaternary ammonium groups to silane or siloxane in organosilicon compound (1) the silane (1) (a) or polydiorganosiloxane (1) (b) may be water-soluble. In such cases the surfactant (3) will be present as an emulsifying aid for maintaining the amino-containing polydiorganosiloxane (2) in the dispersed state.

Components (1) and (2) of the compositions are preferably employed in relatively small proportions e.g. from about 0.025 weight percent based on the total weight of the composition. The most preferred compositions are those comprising from about 0.05 to about 5% by weight of each of (1) and (2) based on the total weight of components (1) to (4). The surfactant component will be present in an amount sufficient to provide the desired stability of the dispersion, generally from about 0.01 to about 5% by weight based on the total weight of (1), (2), (3) and (4). A preferred composition is therefore that comprising
0.05–5.00% by weight of (1)
0.05–5.00% by weight of (2)
0.01–5.00% by weight of (3)
85–99.89% by weight of (4)

In addition to the essential ingredients specified above the compositions may contain other ingredients which are conventional and/or beneficial. Examples of such other ingredients are thickeners and stabilisers e.g. carboxymethyl cellulose, hydroxypropyl cellulose and guar gum, perfumes, bactericides, solvents, preservatives, opacifiers, sequestering agents and conventional hair conditioning agents such as waxes, oils and organic quatenary compounds. In addition the compositions may be formulated as shampoos by the inclusion of suitable detergents for the cleaning of hair, for example those based on fatty alcohols e.g. lauryl and myristyl alcohol, or fatty alcohol ethoxylates. Examples of such detergents are sodium lauryl sulphate, sodium lauryl ether sulphate, ammonium lauryl sulphate and triethanolamine lauryl sulphate. Depending on the nature of the surfactant (3) it may in some cases function both as the dispersing aid for the silicone and as the detergent component of a shampoo formulation. When so formulated the proportion of surfactant (3) will normally be increased over the amount required to provide stability of the dispersion, for example up to about 30% by weight or more based on the total weight of (1), (2), (3) and (4).

The following examples, in which parts are expressed by weight and Me represents the methyl group, illustrate the invention.

EXAMPLE 1

1000 parts of a hydroxyl-terminated polydimethylsiloxane having a viscosity of approximately 4000 cS was reacted with 7 parts of $H_2N(CH_2)_2NH(CH_2)_3Si(CH_3)(OCH_3)_2$ and the resulting polymer (33 parts) emulsified in 63.4 parts water, employing 3.3. parts of an ethylene oxide adduct of trimethylnonanol (Emulsion A). This emulsion (1 part) and the silane $(MeOCH_2CH_2O)_2MeSi(CH_2)_3N^+Me_2(C_{13}H_{27})Cl^-$ (0.35 part) were dispersed in water (98.65 parts) and the resulting dispersion employed to treat tresses of natural European hair by dipping. The treated hair was rinsed once in water at 25° C. and combed. The comb passed easily through the wet hair without snatching.

When the hair had been dried with a hand held hair dryer it possessed body and a silky handle and was easily combed.

EXAMPLE 2

A shampoo composition was prepared by mixing

| | |
|---|---|
| Empicol ESB 70 (sodium lauryl ether sulphate, 68% w/w in water) | 20.0 parts |
| pearling agent | 5.5 parts |
| Empilan 2125 (linoleic diethanolamide) | 3.5 parts |
| Sodium chloride | q.s. |
| Citric acid | q.s. |
| Water to | 100 parts |

To this composition were then added with thorough mixing 0.125 part of the silane and 0.375 part of Emulsion A described in Example 1. The shampoo was employed to wash tresses of natural European hair. After rinsing once in cool water the hair was dried using a conventional hand held hair dryer. The treated hair was found to possess fullness and body. It was also easy to comb when dry, although less so than the tresses treated according to Example 1.

EXAMPLE 3

A shampoo composition was prepared by mixing

| | |
|---|---|
| Empicol ESB 70 (sodium lauryl ether sulphate 68% in water) | 20.0 parts |
| Empicol 0627 (pearling agent) | 5.5 parts |
| Empilan 2125 (linoleic diethanolamide) | 3.5 parts |
| NaCl | 1.0 part |
| Water | 68.65 parts |
| Quaternary siloxane[1] | 0.35 part |
| Amino siloxane[2] | 1.00 part |

[1] The quaternary siloxane was obtained by reacting the silane Me(OMe)$_2$.Si(CH$_2$)$_3$N$^+$Me$_2$(C$_{13}$H$_{22}$)Cl$^-$ (2 mol) with a silanol-terminated polydimethylsiloxane having approximately 10 dimethylsiloxane units (1 mol).
[2] A 37% by weight aqueous emulsion of a trimethyl-siloxy-terminated copolymer having on average per molecule 98Me$_2$SiO units and 2MeSiCH$_2$CH.CH$_3$CH$_2$NHCH$_2$CH$_2$NH$_2$ units (Emulsion B).
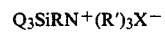

The emulsion was prepared employing an ethylene oxide adduct of trimethylnonanol (2%) and an octyl-phenoxypolyethoxyethanol (4%) as the emulsifying agents.

A control formulation was also prepared for purposes of comparison which was identical with the above formulation except that both siloxanes were omitted.

The shampoo was employed with warm water to wash tresses of natural, brunette, European hair. After rinsing once in cool water the tresses were combed and then dried employing a conventional warm air drier. The ease of combing of the tresses before and after drying was noted. The appearance of the hair after drying and its susceptibility to static build up were also recorded.

| | Wet Comb | Dry Comb | Static* | Appearance |
|---|---|---|---|---|
| Control | Difficult | Difficult | 300% | Normal |
| Shampoo of invention | Fair | Easy | 150% | Silky |

*The static properties were measured by comparing the angles of spread of the extremities of the dry tresses before and after combing.

In addition to a general improvement in the properties listed above hair treated with the siloxane-containing shampoo exhibited additional body (fullness and bulk).

EXAMPLE 4

Four hair conditioner compositions were prepared by mixing the following ingredients:

| | X | Y | Control A | Control B |
|---|---|---|---|---|
| Polawax GP200 (nonionic self-emulsifying wax) | 5.0 | 5.0 | 5.0 | 5.0 parts |
| Water | 94.66 | 94.66 | 94.8 | 93.5 parts |
| Quaternary siloxane[1] | 0.20 | 0.20 | 0.20 | — part |
| Emulsion B[2] | 0.14 | — | — | 1.5 part |
| Emulsion A[3] | — | 0.14 | — | — part |

[1] and [2] As described and employed in Example 3.
[3] As described in Example 1.

The compositions were employed as conditioning agents for the treatment of tresses of natural, brunette, European hair as described in Example 1. The hair was combed, dried and combed again and the ease of combing, static properties and appearance recorded as follows:

| | Wet Comb | Dry Comb | Static | Appearance |
|---|---|---|---|---|
| Control A | Easy | Fair | 250% | Slightly dry |
| Control B | Very Easy | Slight drag | 200% | Silky |
| X | Very easy | Easy | 0% | Silky |
| Y | Very easy | Easy | 0% | Silky |

Tresses treated with compositions X and Y exhibited fullness and body when dry. This property was not present in the tresses treated with the control compositions.

That which is claimed is:

1. A composition for treating the hair to improve the manageability, softness and appearance which comprises (1) from 0.025 to 5% by weight of an organosilicon compound selected from (a) silanes represented by the general formula $$Q_3SiRN^+(R')_3X^-$$

wherein each Q represents an alkyl group having from 1 to 4 carbon atoms, a hydroxyl group, or an alkoxy group or alkoxy-alkoxy group having less than 12 carbon atoms, R represents a divalent organic group having from 3 to 10 carbon atoms selected from the group consisting of aliphatic hydrocarbon radicals, aliphatic hydrocarbon radicals containing ether linkages, hydroxyl-substituted aliphatic hydrocarbon radicals and hydroxyl-substituted aliphatic hydrocarbon radicals containing ether linkages, each R' represents a monovalent hydrocarbon group having from 1 to 18 carbon atoms and X represents a halogen atom, and (b) polydiorganosiloxanes having in the molecule at least one silicon-bonded group represented by the general formula

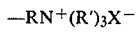

wherein R, R' and X are as hereinabove defined, at least 40 percent of the total silicon-bonded substituents being methyl groups and any remaining substituents being selected from monovalent hydrocarbon groups having from 2 to 8 carbon atoms, hydroxyl groups and alkoxy and alkoxyalkoxy groups having less than 12 carbon atoms, (2) from 0.025 to 5% by weight of a polydiorganosiloxane having in the formula at least one group represented by the general formula

wherein R″ represents an alkylene group having from 3 to 8 inclusive carbon atoms and R‴ represents a hydrogen atom, an alkyl group having from 1 to 4 inclusive carbon atoms or an aliphatic hydrocarbon group attached to the nitrogen atom through a carbon to nitrogen bond and containing at least one group selected from —NH— and —NHZ groups wherein Z represents a hydrogen atom or an alkyl group having from 1 to 4 carbon atoms, at least 50 percent of the total silicon-bonded substituents being methyl groups and any remaining substituents being selected from monovalent hydrocarbon groups having from 2 to 8 carbon atoms, hydroxyl groups and alkoxy and alkoxyalkoxy groups having less than 12 carbon atoms, (3) from 0.01 to 30% by weight of at least one surfactant and (4) from 60 to 99.94% by weight of water.

2. A composition as claimed in claim 1 wherein each Q is selected from the group consisting of methyl, methoxy, ethoxy and methoxyethoxy.

3. A composition as claimed in claim 1 wherein the —R″NHR‴ group is selected from —(CH$_2$)$_3$NH$_2$, —(CH$_2$)$_3$NHCH$_2$CH$_2$NH$_2$ and —CH$_2$CHCH$_3$CH$_2$NHCH$_2$CH$_2$NH$_2$.

4. A composition as claimed in claim 1 wherein (1) and (2) are each present in an amount of from 0.05 to 5% by weight based on the total weight of (1), (2), (3) and (4) in the composition.

5. A hair conditioning agent, comprising the composition of claim 1.

6. A shampoo, comprising the composition of claim 1.

7. A method for treating hair to improve the manageability, softness and appearance which comprises applying thereto a composition as claimed in claim 1.

* * * * *